(12) United States Patent
Garcia Lopez (10) Patent No.: US 11,090,400 B2
(45) Date of Patent: Aug. 17, 2021

(54) AUTOCLAVE WITH AUTONOMOUS INTERNAL STERILISING CHAMBERS FOR STERILISING SANITARY WASTE AND MEDICAL INSTRUMENTS

(71) Applicant: STERIALE SOCIEDAD ANONIMA, Motril (ES)

(72) Inventor: Jose Carlos Garcia Lopez, Motril (ES)

(73) Assignee: Steriale Sociedad Anonima, Motril (ES)

( * ) Notice: Subject to any disclaimer, the term of this patent is extended or adjusted under 35 U.S.C. 154(b) by 154 days.

(21) Appl. No.: 16/323,198

(22) PCT Filed: Jul. 27, 2017

(86) PCT No.: PCT/ES2017/070547
§ 371 (c)(1),
(2) Date: Feb. 4, 2019

(87) PCT Pub. No.: WO2018/024928
PCT Pub. Date: Feb. 8, 2018

(65) Prior Publication Data
US 2019/0167830 A1 Jun. 6, 2019

(30) Foreign Application Priority Data
Aug. 4, 2016 (ES) ............... ES201600664

(51) Int. Cl.
*A61L 2/24* (2006.01)
*A61L 2/20* (2006.01)
*A61L 2/07* (2006.01)

(52) U.S. Cl.
CPC ............... *A61L 2/24* (2013.01); *A61L 2/202* (2013.01); *A61L 2/07* (2013.01); *A61L 2202/11* (2013.01); *A61L 2202/14* (2013.01)

(58) Field of Classification Search
CPC ... A61L 2/24; A61L 2/202; A61L 2/07; A61L 2202/11; A61L 2202/14; A61L 11/00; B02C 19/0075; B09B 3/0075
See application file for complete search history.

(56) References Cited

U.S. PATENT DOCUMENTS 5,266,275 A * 11/1993 Faddis ............... A61L 2/202
422/116
5,486,685 A 1/1996 Dodds
(Continued)

FOREIGN PATENT DOCUMENTS

CN 2378044 5/2000
WO WO 2002/30476 A1 4/2002

OTHER PUBLICATIONS

Gizmodo, "iOS vs Android: The 2015 Edition" (Year: 2015).*
Oct. 23, 2017 International Search Report issued in International Patent Application No. PCT/ES2017/070547.

*Primary Examiner* — Sean E Conley
*Assistant Examiner* — Brendan A Hensel
(74) *Attorney, Agent, or Firm* — Knobbe, Martens, Olson & Bear, LLP (57) ABSTRACT

The present invention relates to a pressurised-vapour autoclave characterised in that, in addition to sterilising instruments in a main chamber, it allows a second or third hermetic, exchangeable sterilising chamber to be housed inside the autoclave and connected, by means of a quick connection, to the main sterilising chamber, thus allowing access to the internal components of the autoclave such as compressors, water heaters, solenoid valves, etc., in order to sterilise sanitary waste without contaminating the main chamber with steam or ozone gas, thereby producing two or three completely autonomous and separate chambers. The present invention also relates to a method for operating the autoclave, wherein the autoclave reports the number of kilos (Continued)

treated by means of weight sensors on the feet of same, as well as all the internal parameters thereof by means of a GPRS-SIM circuit board.

7 Claims, 11 Drawing Sheets

(56) References Cited

U.S. PATENT DOCUMENTS

| | | | |
|---|---|---|---|
| 7,815,851 B1 | 10/2010 | Lewis | |
| 2010/0278688 A1* | 11/2010 | Tanaka | A61L 11/00 422/26 |
| 2012/0313014 A1* | 12/2012 | Stibich | A61L 2/10 250/492.1 |
| 2015/0367008 A1* | 12/2015 | Romo | A61L 2/24 422/24 |
| 2016/0000951 A1* | 1/2016 | Kreiner | A61L 2/10 422/24 |

* cited by examiner

AUTOCLAVE WITH AUTONOMOUS INTERNAL STERILISING CHAMBERS FOR STERILISING SANITARY WASTE AND MEDICAL INSTRUMENTS

CROSS-REFERENCE TO RELATED APPLICATION

This application is a 35 U.S.C. § 371 National Phase Application of PCT Application No. PCT/ES2017/070547 filed Jul. 27, 2017, which claims priority to ES Application No. P201600664 filed Aug. 4, 2016. The disclosure of these prior applications are hereby incorporated by reference herein in their entirety.

OBJECT OF THE INVENTION

The object of the present invention application is to register a system that relates to an autoclave that sterilises with pressurised steam, and which has different internal exchangeable sterilising chambers for sterilising instruments and sanitary waste in the same autoclave, incorporating notable innovations and advantages compared to techniques used hitherto.

In another embodiment, the present invention application relates to an autoclave that sterilises with ozone gas, and which has different internal exchangeable sterilising chambers for sterilising instruments and sanitary waste.

Likewise, the present invention application also relates to an autoclave with at least one main sterilising chamber and at least one second hermetic, exchangeable sterilising chamber, connected and housed inside the main sterilising chamber.

Moreover, the present invention application relates to a pressurised-vapour autoclave characterised in that, in addition to sterilising instruments in a main chamber, it allows a second hermetic, exchangeable sterilising chamber to be housed inside the autoclave and connected, by means of a quick connection, to the main sterilising chamber, thus allowing access to the internal components of the autoclave such as compressors, water heaters, solenoid valves, etc., in order to sterilise sanitary waste without contaminating the main chamber, thereby producing two completely autonomous and separate chambers.

In another embodiment, the present invention application also relates to a pressurised-vapour autoclave characterised in that, in addition to sterilising instruments in a main chamber, it allows a third hermetic, exchangeable sterilising chamber to be housed inside the autoclave and connected, by means of a quick connection, to the main sterilising chamber, thus allowing access to the internal components of the autoclave such as compressors, solenoid valves, ozone lamp, etc., in order to cold sterilise sanitary waste or the medical instrument with ozone gas without contaminating the main chamber. That is, the present invention enables the installation of a third hermetic, exchangeable chamber for cold sterilising instruments with ozone, since there are many medical pieces or objects made of specific material (plastic, etc.), which cannot be sterilised by pressurised-vapour autoclave. In another embodiment, the present invention application relates to an operation method of the autoclave wherein a tray, with the surgical instrument to be sterilised, is inserted in the main chamber. In another embodiment, the present invention application relates to an autoclave system with sterilising chambers and an ozone gas generator, for the sterilisation of the air arriving at the chamber of the sanitary waste.

BACKGROUND

On the current market there are countless vapour autoclaves for sterilising instruments. Similarly, there are vapour autoclaves for sterilising sanitary or pathological waste. Furthermore, it is prohibited by international laws for, in the same autoclave in which the medical instrument is sterilised, sanitary or pathological waste to be sterilised in the same chamber. If the above were to be carried out, the chamber of the medical instruments would be contaminated.

Likewise, an autoclave that previously sterilises the air found inside the sterilising chamber, in order to prevent the outside and circulating air where it the autoclave is located from being contaminated, does not exist in the state of the art. This entails requiring separate rooms with different autoclaves for sterilising sanitary waste and medical instruments.

Problem to be Resolved:

The inventor does not know any autoclave with a single chamber, which sterilises sanitary waste without contaminating the sterilising chamber, and therefore, medical instruments cannot be sterilised in said same chamber without contaminating it. Likewise, the inventor does not know any autoclave that sterilises the air of the sterilising chamber, before expelling it outside, to prevent the contamination of the air of the place where the autoclave is located.

Another problem is that in order to sterilise materials that do not withstand high temperatures, for example, some plastic materials. The same must be sterilised by means of ozone gas. This requires the use of at least two autoclaves for sterilisation using both moist heat and ozone. The inventor does not know any autoclave that sterilises both with moist heat and ozone in the same autoclave.

Solution:

Provide the user with an autoclave that enables, by means of using the same internal components of the autoclave (steam generator, compressor, solenoid valves, chassis, etc.), the sterilisation of both medical instruments and sanitary waste.

Therefore, the present invention provides the user with an autoclave with different exchangeable sterilising chambers, that are completely autonomous and hermetic to the main sterilising chamber of the autoclave, to sterilise sanitary waste by means of moist heat or pressurised vapour.

In addition, the present invention provides the user with an autoclave with exchangeable sterilising chambers, that are completely autonomous and hermetic to the main sterilising chamber of the autoclave, to cold sterilise sanitary waste with ozone.

The present invention provides the user with an autoclave with a sterilising chamber, that is completely autonomous and hermetic for cold sterilisation with ozone gas for the air contaminated coming from the chamber of the sanitary waste, as well for the sterilisation of surgical waste or materials themselves.

DESCRIPTION OF THE INVENTION

The present invention describes an autoclave for sterilising medical instruments and sanitary waste. Likewise, the present invention describes an autoclave for sterilising medical instruments and sanitary waste by means of ozone gas.

Similarly, the present invention describes an autoclave for sterilising medical instruments and sanitary waste by means of moist heat.

The present invention also relates to a hermetic, exchangeable sterilising chamber that has at least one quick connection to connect to the internal components of an autoclave.

Likewise, the present invention also relates to a hermetic, exchangeable sterilising chamber that has at least one sensor.

In another embodiment, the present invention also relates to a hermetic, exchangeable sterilising chamber that has at least one sensor that can be a temperature, pressure, weight, volume, diameter, bacteria, microorganism, virus, moisture, voltage, amperage, air flow, magnetic sensor, etc.

The sanitary waste can comprise water, gases, gloves, infected plastic pieces, infectious materials, etc. In order to suitably handle sanitary waste, an authorised manager must be contracted since there is an applicable regulation for each country that indicates that waste cannot be disposed of without prior sterilisation. The foregoing is to prevent sources of infection.

The autoclave of the present invention prevents the need to contract a sanitary waste manager since the autoclave has a second hermetic, exchangeable sterilising chamber where the sanitary waste is to be housed.

The present invention enables the sterilisation of both sanitary waste and medical instruments in the same autoclave without contaminating the latter. In a first embodiment, the present invention describes an autoclave for sterilising medical instruments in the main chamber thereof and also a second function of the autoclave through a quick connection housed inside the main chamber to connect a second exchangeable sterilising chamber that is completely autonomous and hermetic in order to eliminate pathological waste.

In another embodiment, the present invention relates to an autoclave with a main sterilising chamber for sterilising instruments, which has: at least one quick connection with a systems of independent ozone gas inlets and outlets that is housed inside the main sterilising chamber and that connects to the internal components of the autoclave;
  at least one second hermetic, exchangeable sterilising chamber for waste or instruments, which is housed inside the chamber for sterilising pathological waste, without contaminating the main sterilising chamber with ozone gas;
  at least one weight sensor, to weigh the sanitary waste to be sterilised; and
  at least one electronic system to generate waste sterilisation reports.

In another embodiment, the present invention relates to a pressurised-vapour autoclave with a main sterilising chamber for sterilising instruments, which has: at least one quick connection with a system of independent water and vapour inlets and outlets that is housed inside and in the centre of the main sterilising chamber and that connects to the internal components of the autoclave;
  at least one second hermetic, exchangeable sterilising chamber for waste with a male quick connection, which is housed inside and in the centre of the chamber for sterilising pathological waste, without contaminating the main sterilising chamber with pressurised vapour;
  at least one weight sensor, to weigh the medical waste to be sterilised; and
  at least one electronic system to generate waste sterilisation reports.

In another embodiment, the present invention relates to an autoclave, which comprises:
  a main sterilising chamber; at least one quick connection housed inside the main sterilising chamber that has a system of independent inlets and outlets which connect to the internal components of the autoclave;
  at least one hermetic, exchangeable sterilising chamber with quick connection, which connects to the quick connection housed inside the main sterilising chamber;
  at least one ozone sterilisation system;
  at least one moist heat sterilisation system;
  at least one weight sensor, to weigh the sanitary waste to be sterilised; and
  at least one electronic system to generate waste sterilisation reports.

In another embodiment, the present invention relates to an autoclave that, by means of an ozone sterilising system, sterilises the air of the sterilising chamber.

In another embodiment, the present invention describes an autoclave that has an electronic system for generating waste sterilisation reports, which in turn has:
  at least one circuit board installed in the Key board of the autoclave, which enables the sterilisation statuses that the autoclave reports at the end of each cycle to be reported via GPRS;
  at least one circuit board installed in the Key board of the autoclave, which enables the autoclave to be activated or deactivated by means of a SMS message from the SIM card thereof;
  at least one circuit board installed in the Key board of the autoclave, which enables the weight of the rubbish inserted inside the second exchangeable sterilising chamber of the autoclave to be reported by means of the sensors in the legs of the autoclave.

In another embodiment, the autoclave of the present invention has a sterilising system of the air housed inside the second exchangeable sterilising chamber.

The air sterilising system consists of a lamp generating ozone gas and pipe conduits that connect the autoclave to the second exchangeable sterilising chamber by means of quick connections.

The ozone gas generated in the autoclave travels through the pipe conduits and passes through the quick connections until it reaches the inside of the second exchangeable sterilising chamber. The ozone gas oxidises the bacteria that are found in the air contained by the second exchangeable sterilising chamber, meaning that the air is sterilised before being expelled from the chamber. This prevents the contamination of the air outside the autoclave, that is, it prevents the contamination of the room in which the autoclave is housed.

The above prevents the proliferation of microorganisms, bacteria, viruses, parasites, fungi, etc., due to air contamination in the sterilisation chamber. Likewise, it is allowed to be housed in the same room in which medical instruments sterilised by the autoclave are found, due to the fact that the non-contamination of the air in the room in which the autoclave is housed is ensured.

Moreover, the quick connections that are described in the present invention have sensors, such as temperature, weight, volume, diameter sensors, etc. In another embodiment, the autoclave of the present invention has a main sterilising chamber for sterilising instruments, wherein medical instruments to be sterilised are inserted on staggered trays of the main sterilising chamber.

In another embodiment, the present invention also relates to a method for sterilising sanitary waste in a moist heat autoclave, preferably class B pressurised vapour (vacuum pump).

In another embodiment, the present invention also relates to a method for sterilising sanitary waste in a moist heat autoclave, preferably ozone gas.

DESCRIPTION OF A PREFERRED EMBODIMENT

Figure 1:
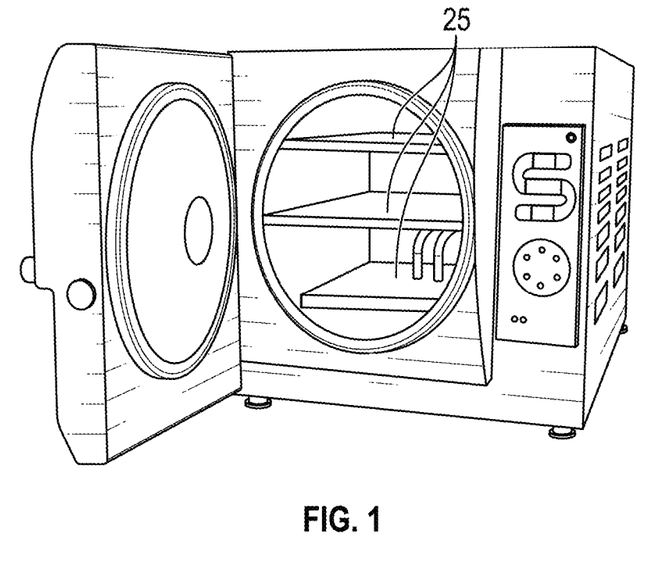
FIG. 1. shows an embodiment of the autoclave according to the present invention.

As shown schematically in FIG. 1, the autoclave has trays (25) housed in the main chamber thereof to deposit the medical instruments for their sterilisation.

1st Novelty of the Invention

Second hermetic, exchangeable sterilising chamber for pressurised-vapour sterilisation of bio-sanitary waste.

Figure 2:
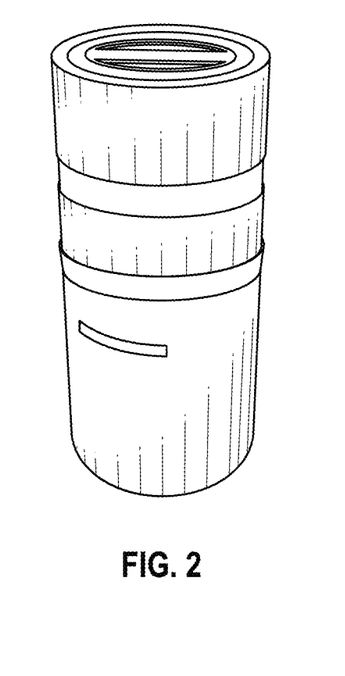
FIG. 2. shows an embodiment of a second exchangeable sterilising chamber for sterilising sanitary waste according to the present invention.
Figure 3:
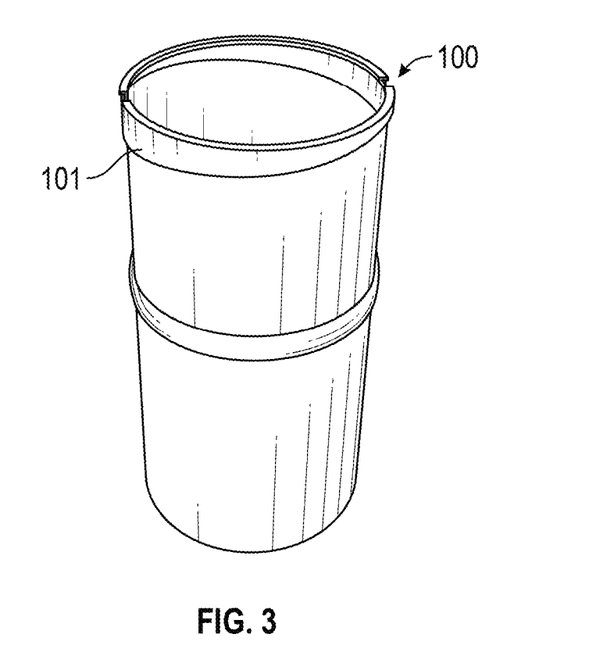
FIG. 3. shows the thread-shaped grooves that the chamber has on the upper and outer edge thereof.

Independently of this main chamber, the autoclave uses another second exchangeable sterilising chamber, FIG. 2, for sterilising bio-sanitary waste. The method for sterilising sanitary waste comprises: filling the second exchangeable sterilising chamber with sanitary waste, closing the second exchangeable sterilising chamber with a lid, which has at the ends thereof opposite the diameter, two lower tabs that will connect with the thread-shaped grooves that the chamber has on the upper and outer edge thereof, FIG. 3, turning the lid in a clockwise direction until a half turn is completed and the lid is thus hermetically closed since the lid is threaded by the downwards action of the grooves when it is turned. FIG. 3 shows the start of the half thread (100) and the end of the half thread (101) of the upper edge of the chamber.

Figure 4:
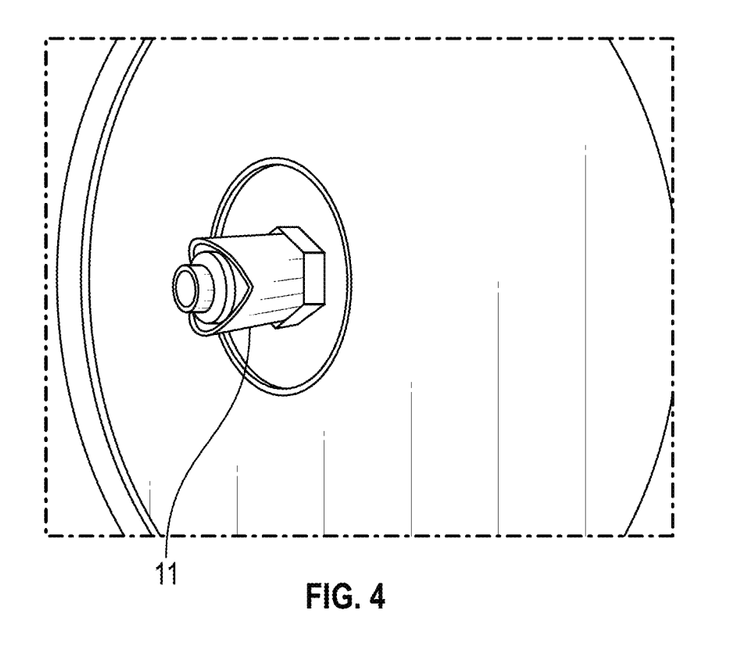
FIG. 4. shows an embodiment of the second exchangeable sterilising chamber with a male quick connection at the base thereof according to the present invention.
Figure 5:
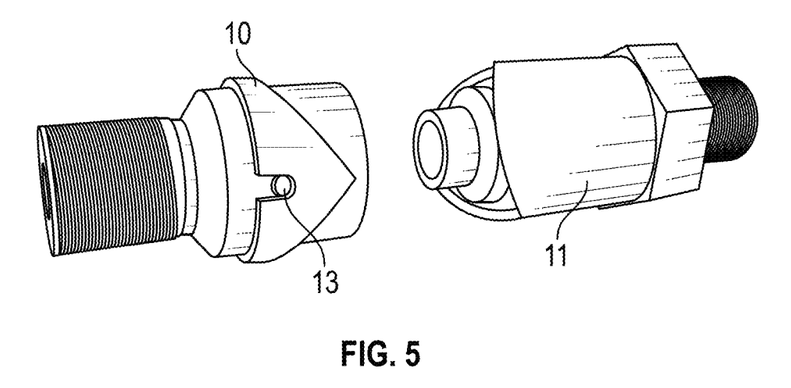
FIG. 5. shows an embodiment of a male quick connection and a female quick connection according to the present invention.
Figure 6:
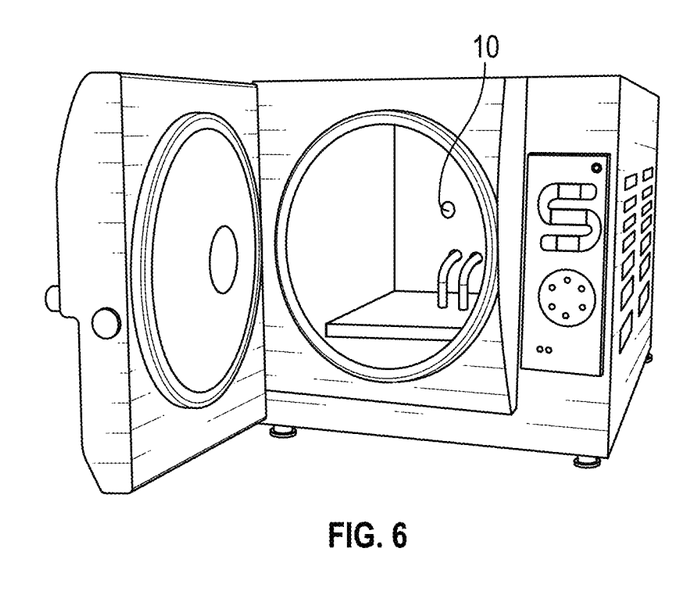
FIG. 6. shows the main sterilising chamber with the female quick connection thereof of an embodiment of the autoclave according to the present invention.

The second exchangeable sterilising chamber has at the base thereof a male quick connection (11), FIG. 4, to connect to the main chamber of the autoclave through the female quick connection (10), FIGS. 5 and 6. By means of this connection, the second hermetic, exchangeable sterilising chamber and the autoclave communicate for the inlet and outlet of air, water and water vapour.

Figure 15:
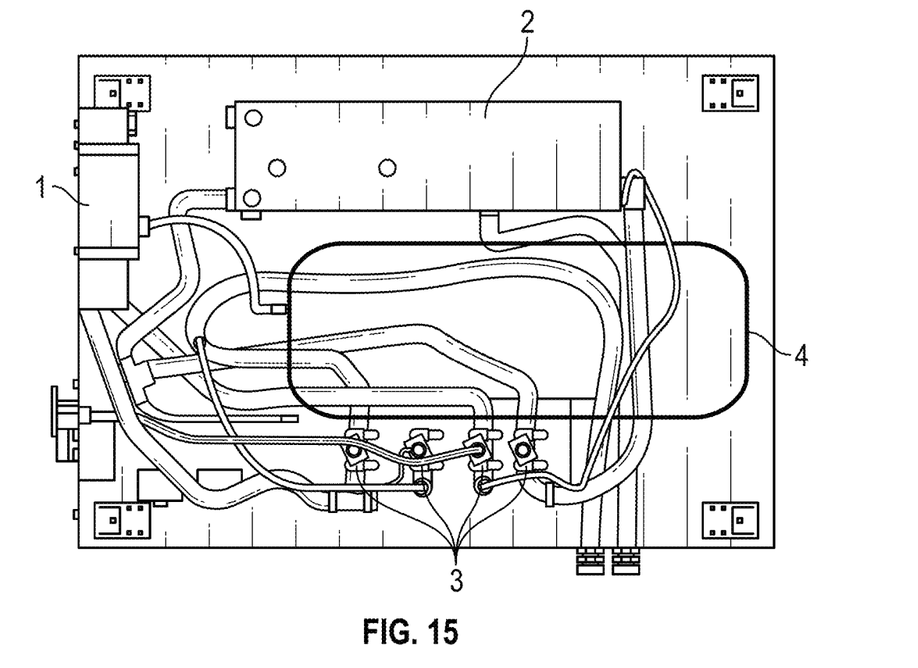
FIG. 15. schematically shows the conduits, solenoid valves and other components of an embodiment of the autoclave according to the present invention.
Figure 16:
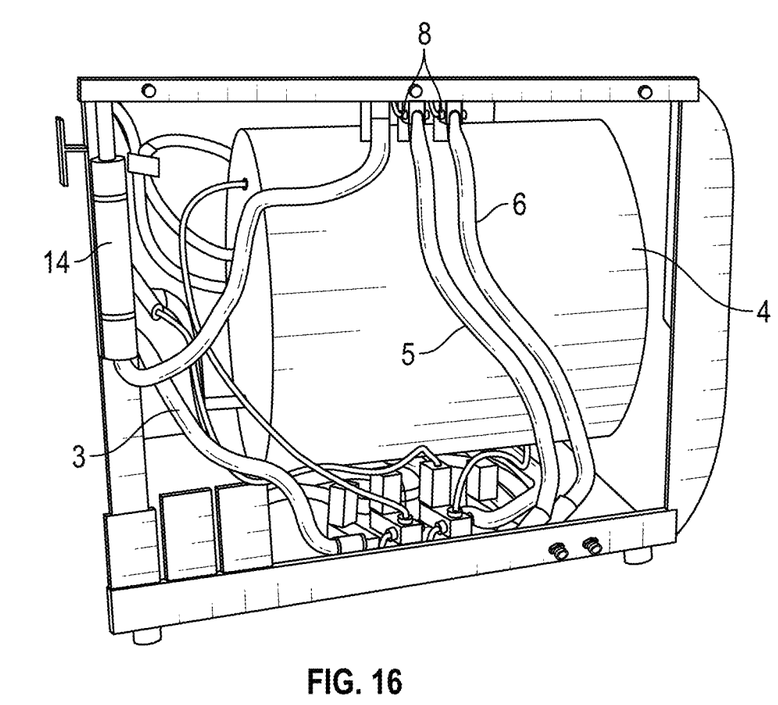
FIG. 16. shows a perspective view of the internal components of an embodiment of the autoclave according to the present invention.
Figure 17:
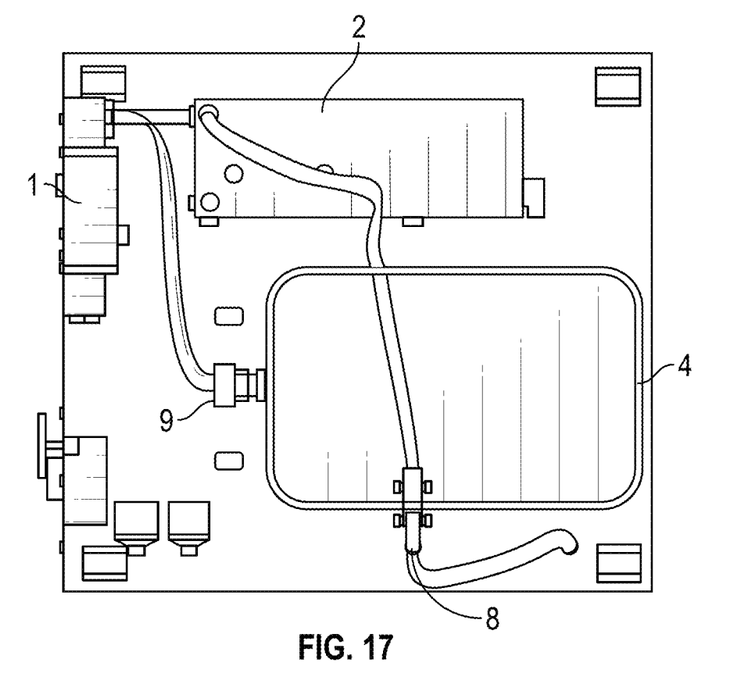
FIG. 17. schematically shows the conduits, solenoid valves and other components of an embodiment of the autoclave according to the present invention.
Figure 18:
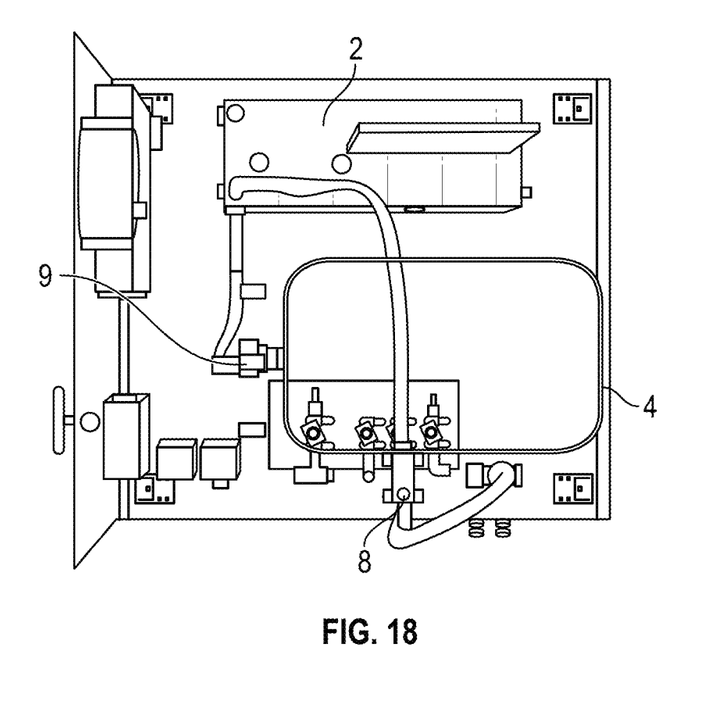
FIG. 18. schematically shows the conduits, solenoid valves and other components of an embodiment of the autoclave according to the present invention.

As can be seen in FIG. 15, the autoclave has conduits and solenoid valves for the inlet and outlet of air, water and water vapour (3), which are linked with a water heater (1) and a compressor (2) to the main chamber thereof (4) for when it sterilises the medical instruments housed on the trays thereof, and independent to the conduits used by the main sterilising chamber, as shown in FIGS. 16, 17 and 18, other independent conduits for the inlet and outlet of air, water and water vapour (5 and 6), actuated by independent solenoid valves (8) and through the quick connection of the main chamber, thus enabling the content of the second exchangeable sterilising chamber of the waste to be sterilised without contaminating the main chamber of the autoclave.

Figure 7:
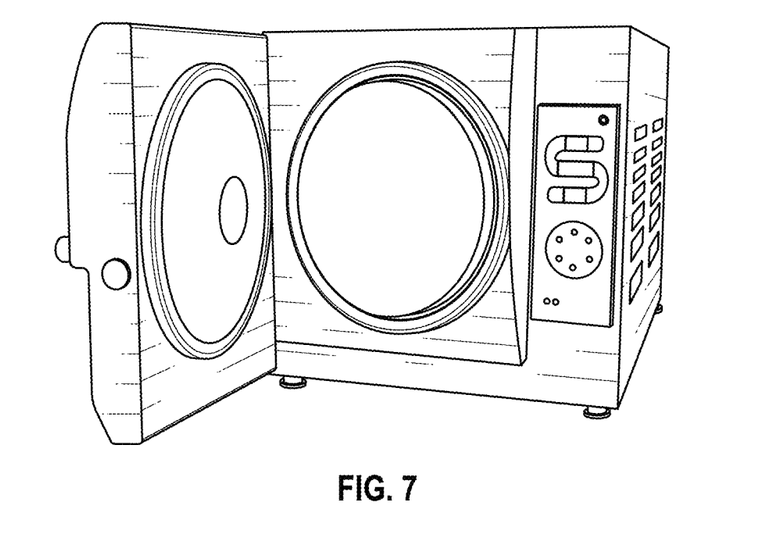
FIG. 7. shows a second sterilising chamber housed by means of the quick connection in the main chamber of an embodiment of the autoclave according to the present invention.

Once the second hermetic, exchangeable sterilising chamber of the waste is housed by means of the quick connection to the main chamber of the autoclave, FIG. 7, the quick connection through the diameter sensor (13) thereof, the start of the sterilisation process of the autoclave for waste of the second chamber thereof is activated.

2nd Novelty of the Invention

Weight sensors in the legs of the autoclave to weigh the pathological waste of the hermetic, exchangeable sterilising chamber.

There is no autoclave for pathological waste on the market that weighs the rubbish that has been sterilised, to thus track the operation thereof, and it is for this reason that we have designed a system of weight sensors in the legs of the autoclave that will send us the information of the kilos or pounds treated by our equipment.

Figure 11:
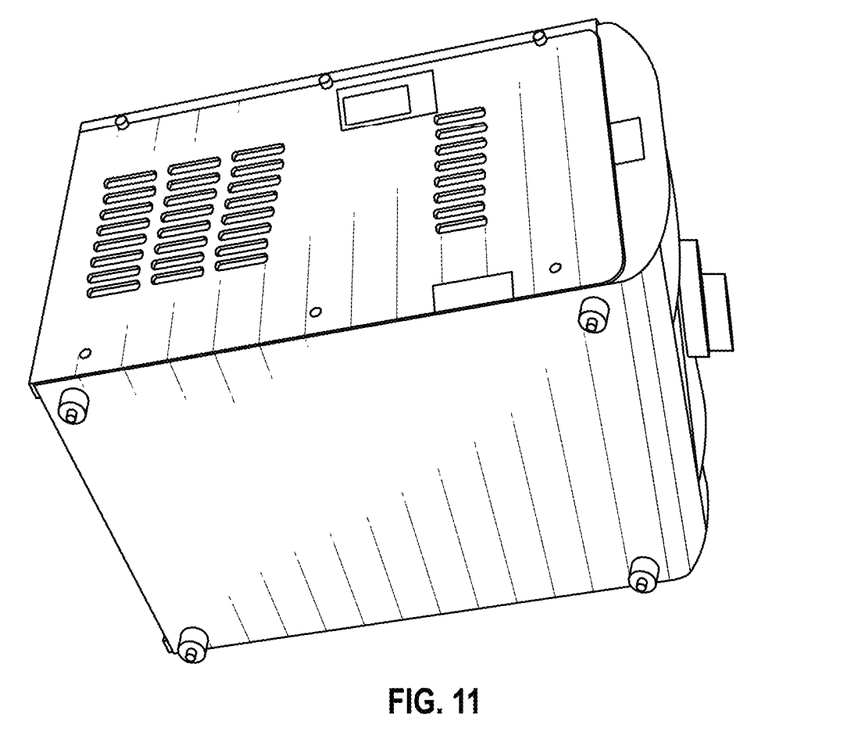
FIG. 11. shows a perspective view of an embodiment of the autoclave according to the present invention.
Figure 12:
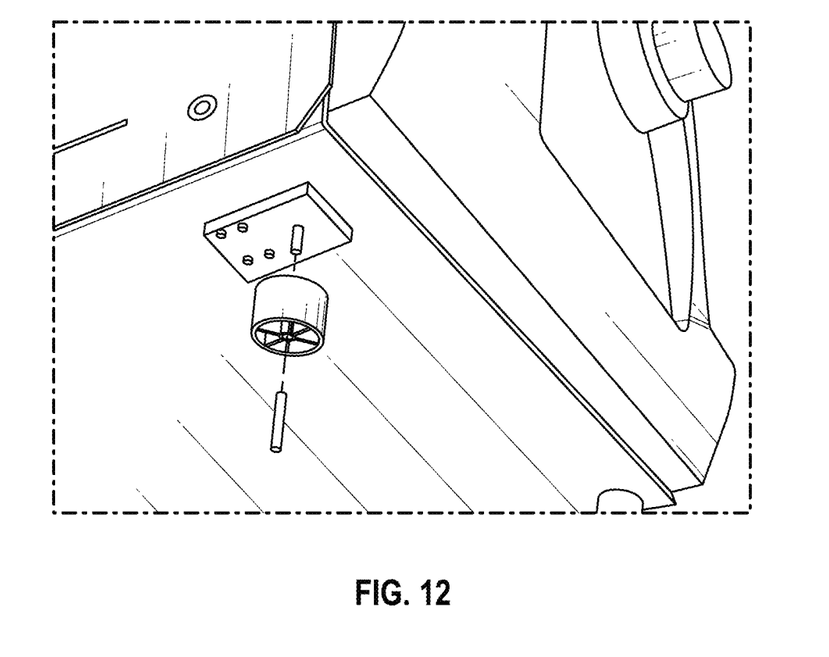
FIG. 12. shows an exploded perspective view of a sensor in one of the legs of an embodiment of the autoclave according to the present invention.
Figure 20:
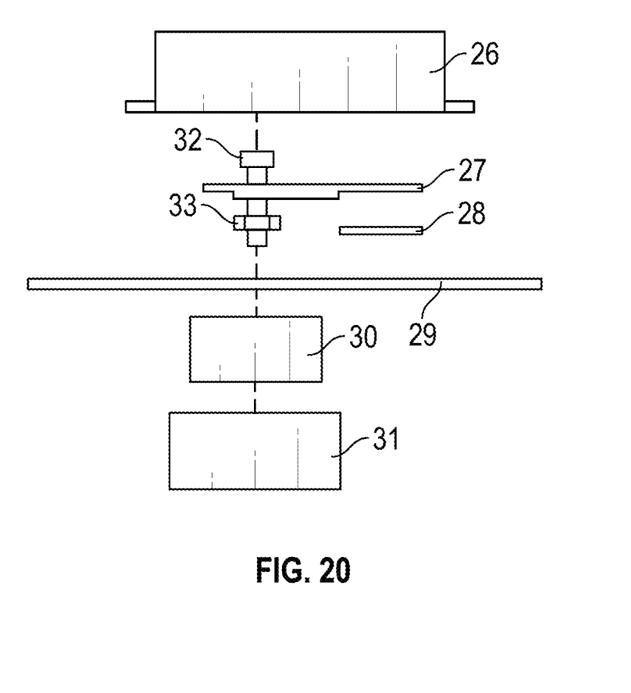
FIG. 20. shows a diagram of the parts that make up a weight sensor according to the present invention.

The first parameter that the autoclave will evaluate will be the weight of the content of the second hermetic, exchangeable sterilising chamber through the sensors in the four legs of the autoclave, FIGS. 11 and 12. A diagram of the parts that make up the weight sensor as shown in FIG. 20.

26.—Protector of the weight sensor.
27.—Weight sensor.
28.—Reference plate.
29.—Lower support plate of the chassis of the autoclave.
30.—Leg of the autoclave.
31.—Protector for transport.
32.—Screw.
33.—Nut.

Figure 21:
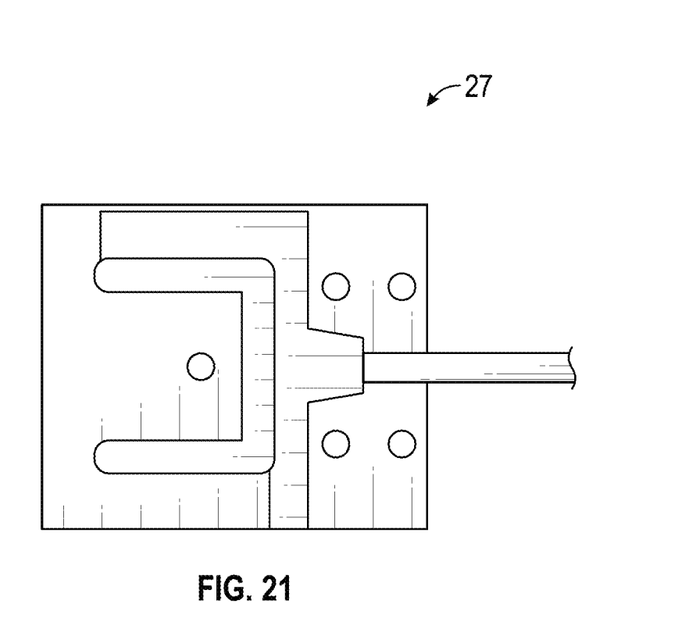
FIG. 21. shows a detailed view of the weight sensor with wiring that goes to the key board.

The weight sensor operates due to the bending between the contact parts of the reference plate (28) and the weight sensor (27). According to the pressure exerted on the leg of the autoclave, the sensor transmits a different voltage between the two plates. FIG. 21 shows a detailed view of the weight sensor (27) with wiring that goes to the key board.

3rd Novelty of the Invention

Circuit board housed in the front panel of the autoclave that reports the inner parameters of the autoclave via GPRS-SIM. Similarly, we will need a system that provides us with tracking of what the autoclave does with the waste, as this is required by law, otherwise we would not be certain that the sterilisation of the waste was carried out correctly.

Figure 13:
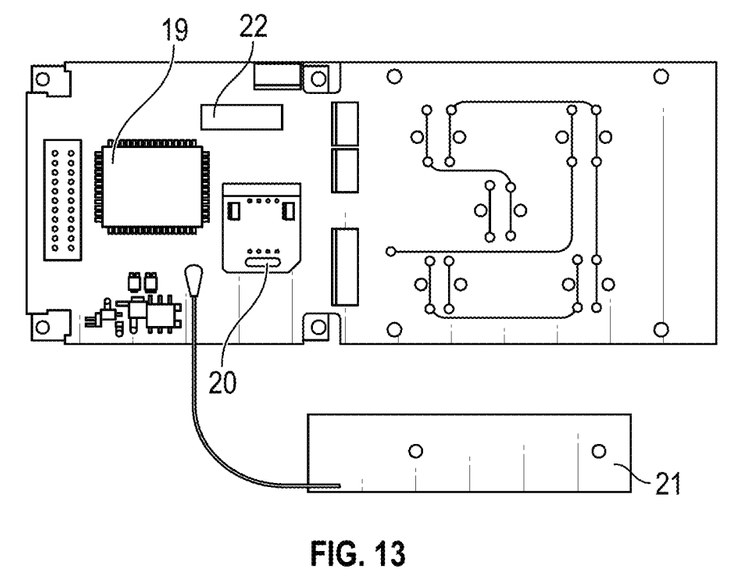
FIG. 13. shows the rear portion of the circuit board of the front panel of an embodiment of the autoclave according to the present invention.
Figure 14:
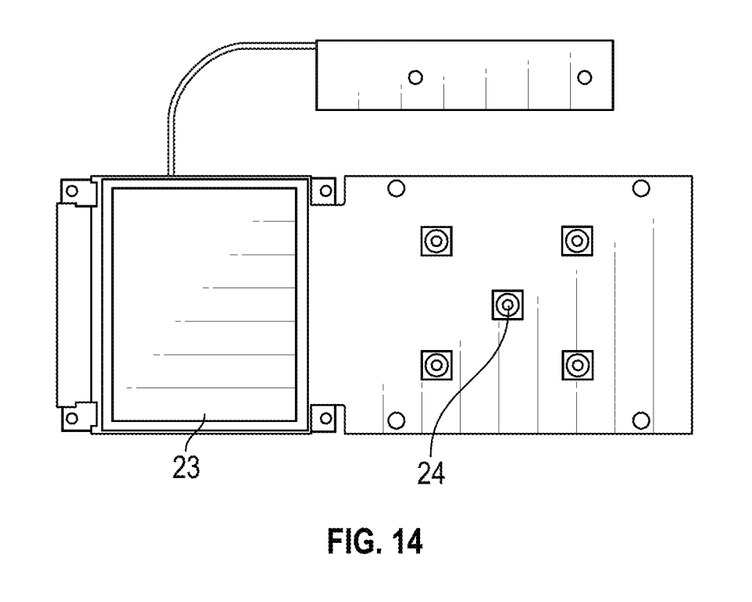
FIG. 14. shows the front portion of the circuit board of the front panel of an embodiment of the autoclave according to the present invention.

This information shall be reported to the circuit board of the front panel, FIGS. 13 and 14, so that through the antenna (21), GPRS module (19) and SIM card (20) thereof it transmits through the chip (22) thereof, SMS messages regarding:

Weight of the waste.
Calendar of the sterilisation system.—Temperatures and pressure inside the chamber.
Sterilisation cycles.
Sterilisation efficiency report.
Possible malfunctions or incorrect operation of the autoclave.

All this data can be downloaded through a specifically-designed platform on the Internet. The present invention enables sterilisation and handling reports of all the operations of the autoclave to be carried out by means of platforms for PC, Android, IOS and PLC.

4th Novelty of the Invention

Third hermetic, exchangeable sterilising chamber for cold sterilisation of medical instruments or waste with ozone.

Figure 10:
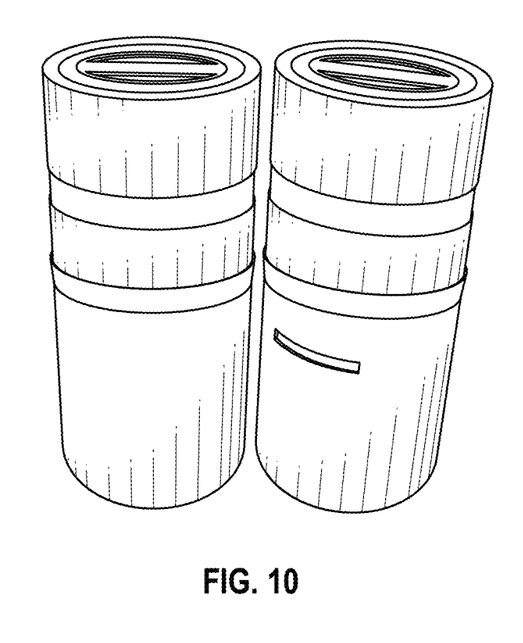
FIG. 10. shows two hermetic, exchangeable sterilising chambers according to the present invention, one being for the sterilisation of biological material and the other for sterilisation by means of ozone.

Similarly, this autoclave will have a third hermetic, exchangeable sterilising chamber, FIG. 10, with the same closure characteristics of the lid thereof as the second chamber of the waste for housing therein medical waste or instruments to sterilise it with ozone gas.

Figure 8:
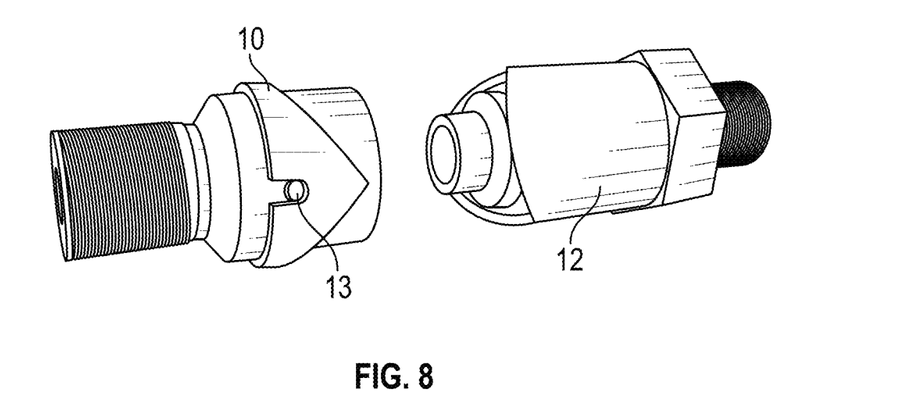
FIG. 8. shows a male quick connection for an ozone chamber and a female quick connection according to the embodiment of the present invention.
Figure 9:
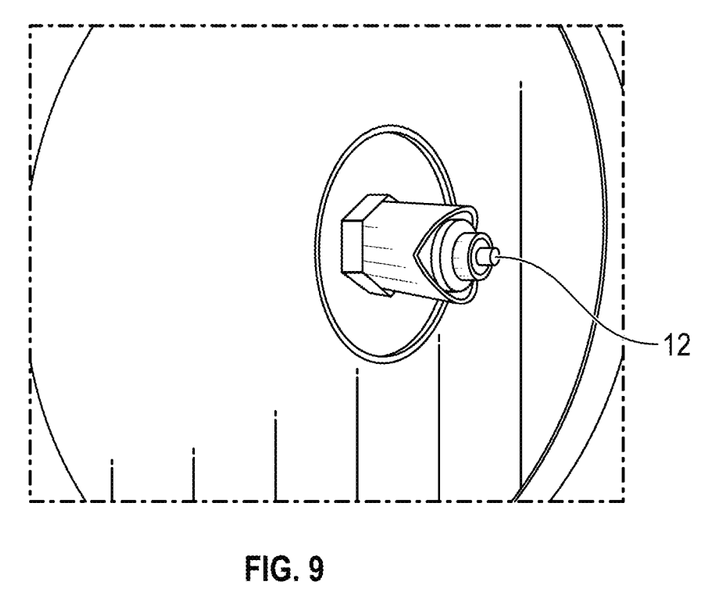
FIG. 9. shows a hermetic, exchangeable sterilising chamber for ozone with a male quick connection in the base thereof according to an embodiment of the present invention.
Figure 19:
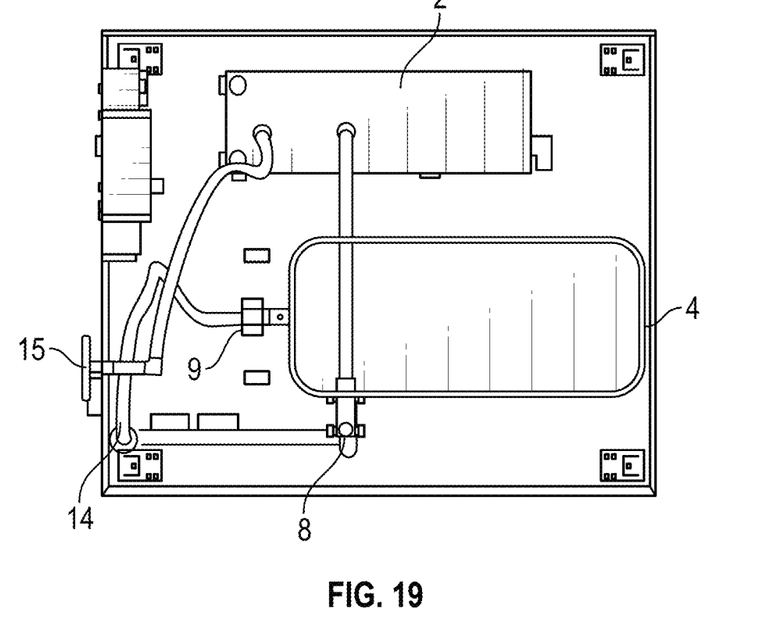
FIG. 19. schematically shows the conduits, solenoid valves and other components for sterilisation by means of ozone in an embodiment of the autoclave according to the present invention.

This third hermetic, exchangeable sterilising chamber, similarly to the second chamber, will also use in the base thereof a quick connection, FIGS. 8 and 9, which unlike the quick connection of the second chamber, the male connection will have a diameter that is smaller than the central shaft (12) thereof so that the female connection housed in the main chamber detects it through the diameter sensor (13) as shown in FIG. 8; thus indicating that it is the chamber for ozone. This third chamber would also use its own internal circuit and solenoid valves (8) of the autoclave with regards to pipes and other components such as a filter (15), a valve generating ozone gas (14) and sharing the same compressor (2) as shown in FIG. 19. As such, this third chamber cold sterilises the content thereof through the rear portion (9) of the quick connection, such as solid waste or medical instruments.

The internal components of the autoclave are used, such as: compressor, chassis, inner circuit, electronics, etc., for the installation of a third hermetic, exchangeable sterilising chamber for the cold sterilisation with ozone of waste or instruments since there are many medical pieces or objects made of a specific material (plastics, etc.) that cannot be sterilised by pressurised-vapour autoclave. Similarly, this system enables us to sterilise the air inside the hermetic, exchangeable sterilising chamber with ozone gas. Similarly, this entire sterilisation process with ozone would be transmitted by the key board described above.

The hermetic, exchangeable sterilising chambers can be manufactured with aluminium. Likewise, the exchangeable sterilising chambers can receive a Teflon treatment that prevents the proliferation of microorganisms in the container or the sanitary waste from adhering to the inner portion of said container.

The hermetic, exchangeable sterilising chambers can have an outer silicone cover to protect them from falls.

The invention claimed is:

1. An autoclave, comprising:
   a main sterilising chamber;
   at least one female quick-connection housed inside the main sterilising chamber that has a system of independent inlets and outlets which connect to internal components of the autoclave;
   a second hermetic, exchangeable sterilising chamber with a male quick-connection, which is configured to connect to the female quick-connection inside the main sterilising chamber;
   a third hermetic, exchangeable sterilising chamber with a male quick-connection configured to connect to the female quick-connection inside the main sterilising chamber and having a diameter smaller than a central shaft thereof so that the female quick-connection of the main sterilizing chamber detects a presence of the male quick-connection through a diameter sensor present in the female quick-connection to indicate that the third hermetic, exchangeable sterilising chamber is present;
   at least one ozone sterilisation system configured to connect to the third hermetic, exchangeable sterilising chamber;
   at least one moist heat sterilisation system configured to connect to the main sterilising chamber and the second hermetic, exchangeable sterilising chamber;
   at least one weight sensor, to weigh sanitary waste to be sterilised; and
   at least one electronic system to generate waste sterilisation reports.

2. The autoclave, according to claim 1, wherein the ozone sterilising system is configured to sterilise air of the third hermetic, exchangeable sterilising chamber.

3. The autoclave, according to claim 1, wherein the electronic system for generating waste sterilisation reports has:
   at least one circuit board installed in a front panel of the autoclave, which enables the sterilisation statuses that the autoclave reports at the end of each cycle to be reported via general packet radio service (GPRS);

at least one circuit board installed in the front panel of the autoclave, which enables the autoclave to be activated or deactivated by means of a SMS message from a SIM card thereof;

at least one circuit board installed in the front panel of the autoclave, which enables the weight of rubbish inserted inside the second exchangeable sterilising chamber of the autoclave to be reported by sensors in the legs of the autoclave.

4. The autoclave, according to claim 3, wherein the electronic system for generating waste sterilisation reports enables sterilisation and handling reports to be carried out on all the functions of the autoclave by controlling a programmable logic controller (PLC) via platforms for PC, Android or IOS.

5. The autoclave, according to claim 2, wherein the ozone sterilisation system comprises a lamp generating ozone gas that has:

at least some pipe conduits connected to the third hermetic, exchangeable sterilising chamber of the sanitary waste so that due to the effects of the ozone gas, the bacteria in the air are oxidised, thus preventing the air that is evacuated to the outside of the autoclave from being contaminated.

6. The autoclave, according to claim 1, wherein the male or the female quick-connection has sensors.

7. A method of sterilising the air of the third hermetic, exchangeable sterilising chamber of an autoclave according to claim 1, comprising:

connecting the male quick-connector of the third hermetic, exchangeable sterilising chamber to the female quick-connector of the main sterilising chamber;

detecting presence of the male quick-connector of the third hermetic, exchangeable sterilising chamber by the diameter sensor of the female quick-connector of the main sterilising chamber, thereby indicating the presence of the third hermetic, exchangeable sterilising chamber; and activating the ozone sterilization system to deliver ozone to the third hermetic, exchangeable sterilising chamber, thereby sterilising the air of the third hermetic, exchangeable sterilising chamber.

\* \* \* \* \*